(12) United States Patent
Elangovan et al.

(10) Patent No.: US 8,975,429 B2
(45) Date of Patent: Mar. 10, 2015

(54) METHOD OF PRODUCING CYCLOHEXASILANE COMPOUNDS

(75) Inventors: Arumugasamy Elangovan, Fargo, ND (US); Kenneth Anderson, Fargo, ND (US); Philip R. Boudjouk, Fargo, ND (US); Douglas L. Schulz, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 381 days.

(21) Appl. No.: 13/522,289

(22) PCT Filed: Jan. 25, 2011

(86) PCT No.: PCT/US2011/022360
§ 371 (c)(1),
(2), (4) Date: Jul. 13, 2012

(87) PCT Pub. No.: WO2011/094191
PCT Pub. Date: Aug. 4, 2011

(65) Prior Publication Data
US 2012/0294791 A1    Nov. 22, 2012

Related U.S. Application Data

(60) Provisional application No. 61/299,287, filed on Jan. 28, 2010, provisional application No. 61/311,118, filed on Mar. 5, 2010.

(51) Int. Cl.
*C07F 7/08* (2006.01)
*C01B 33/04* (2006.01)

(52) U.S. Cl.
CPC ..................................... *C01B 33/04* (2013.01)
USPC ........................................................ 556/406

(58) Field of Classification Search
CPC ......... C07F 7/12; C07F 7/0818; C07F 7/0807
USPC ........................................................ 556/406
See application file for complete search history.

(56) References Cited

U.S. PATENT DOCUMENTS

| | | | |
|---|---|---|---|
| 3,044,845 A | 7/1962 | Jex et al. | |
| 4,038,371 A | 7/1977 | Marin | |
| 4,447,633 A | 5/1984 | Boudjouk | |
| 4,657,777 A | 4/1987 | Hirooka et al. | |
| 4,683,147 A | 7/1987 | Eguchi et al. | |
| 4,695,331 A | 9/1987 | Ramaprasad | |
| 4,746,752 A | 5/1988 | Lepage et al. | |
| 4,827,009 A | 5/1989 | Boudjouk | |
| 4,841,083 A | 6/1989 | Nagai et al. | |
| 4,910,153 A | 3/1990 | Dickson | |
| 5,026,533 A | 6/1991 | Matthes et al. | |
| 5,942,637 A * | 8/1999 | Boudjouk et al. | 556/424 |
| 6,503,570 B2 | 1/2003 | Matsuki et al. | |
| 6,518,087 B1 | 2/2003 | Furusawa et al. | |
| 6,527,847 B1 | 3/2003 | Matsuki | |
| 6,541,354 B1 | 4/2003 | Shimoda et al. | |
| 6,743,738 B2 | 6/2004 | Todd | |
| 6,767,775 B1 | 7/2004 | Yudasaka et al. | |
| 6,846,513 B2 | 1/2005 | Furusawa et al. | |
| 7,052,980 B2 | 5/2006 | Aoki | |
| 7,067,069 B2 | 6/2006 | Shiho et al. | |
| 7,173,180 B2 | 2/2007 | Shiho et al. | |
| 7,223,802 B2 | 5/2007 | Aoki et al. | |
| 7,314,513 B1 | 1/2008 | Zurcher et al. | |
| 7,422,708 B2 | 9/2008 | Kunze et al. | |
| 7,485,691 B1 | 2/2009 | Guo et al. | |
| 7,491,782 B1 | 2/2009 | Guo et al. | |
| 7,498,015 B1 | 3/2009 | Kunze et al. | |
| 7,531,588 B2 | 5/2009 | Weller et al. | |
| 7,553,545 B2 | 6/2009 | Kunze et al. | |
| 7,674,926 B1 | 3/2010 | Guo et al. | |
| 7,723,457 B1 | 5/2010 | Guo et al. | |
| 7,767,261 B2 | 8/2010 | Kunze et al. | |
| 7,799,302 B1 | 9/2010 | Kunze et al. | |
| 7,879,696 B2 | 2/2011 | Kunze et al. | |
| 7,943,721 B2 | 5/2011 | Dioumaev | |
| 7,951,892 B1 | 5/2011 | Guo et al. | |
| 2001/0021760 A1 | 9/2001 | Matsuki et al. | |
| 2003/0229190 A1 | 12/2003 | Aoki et al. | |
| 2005/0145163 A1 | 7/2005 | Matsuki et al. | |
| 2006/0185712 A1 | 8/2006 | Shiho et al. | |

(Continued)

FOREIGN PATENT DOCUMENTS

WO    WO 00/59014    10/2000

OTHER PUBLICATIONS

International Search and Written Opinion for PCT/US2011/022360, mail date Apr. 11, 2011, 6 pages.
Amberger et al., "The Preparation of Trisilylphosphine," Angew. Chem. Int. Ed. Engl., vol. 1, 1962, No. 1, p. 52.
Anderson, "n-Butylhalosilanes, Determination of Silane Hydrogen in Liquids," Contribution from the Chemistry Department, Drexel Institute of Technology, Mar. 20, 1060, pp. 1323-1325.
Choi et al., "Amine-Promoted Disproportionation and Redistribution of Trichlorosilane: Formation of Tetradecachlorocyclohexasilane Dianion," Journal of American Chemical Society, vol. 123, pp. 8117-8118 (2001).
Fritz et al., "Silylphosphanes: Developments in Phosphorus Chemistry," Chem. Rev. 2000, vol. 100, pp. 3341-3401.
Gaines et al., "Synthesis of Bis(pentaboranyl)-Group IV Compounds," Inorganic Chemistry, vol. 13, No. 12, 1974, pp. 2792-2796.
Gokhale et al., "Disilanylphosphine and Dsilylphosphine," Inorganic Chemistry, 1964, vol. 3 (8), pp. 1141-1143.

(Continued)

*Primary Examiner* — Sudhakar Katakam
*Assistant Examiner* — Kofi Adzamli
(74) *Attorney, Agent, or Firm* — Foley & Lardner LLP

(57) ABSTRACT

A method of preparing a cyclohexasilane compound from trichlorosilane is provided. The method includes contacting trichlorosilane with a reagent composition to produce a compound containing a tetradecahalocyclohexasilane dianion, such as a tetradecachlorocyclohexasilane dianion. The reagent composition typically includes (a) tertiary polyamine ligand; and (b) a deprotonating reagent, such as a tertiary amine having a pKa of at least about 10.5. Methods of converting the tetradecahalocyclohexasilane dianion-containing compound to cyclohexasilane or a dodecaorganocyclohexasilane are also provided.

20 Claims, No Drawings

(56) References Cited

U.S. PATENT DOCUMENTS

2006/0281841 A1* 12/2006 Weller et al. .................. 524/261
2012/0294791 A1 11/2012 Elangovan et al.

OTHER PUBLICATIONS

Gollner et al., "Linear and Cyclic Polysilanes Containing the Bis(trimethylsilyl)amino Group: Synthesis, Reactions and Spectroscopic Characterization," Inorganic Chemistry, vol. 42, No. 15, 2003, pp. 4579-4584.

Han et al., "Printed Silicon as Diode and FET Materials—Preliminary Results," Journal of Non-Crystalline Solids, vol. 354, 2008, pp. 2623-2626.

Han et al., "Doped and Undoped Si Films Made from Cyclohexasilane," Spring 2008 Materials Research Society Meeting, San Francisco, CA, Mar. 25, 2008, 1 page.

Hengge et al., "Preparation of Cyclohexasilane, $Si_6H_{12}$," Angew, Chem. Int. Ed. Engl., vol. 16, 1977, No. 6, p. 403.

Herzog et al., "Preparation of Oligosilanes Containing Perhalogenated Silyl Groups and their Hydrogenation by Stannanes," Journal of Organometallic Chemistry 544, 1997, pp. 217-223.

Holbling et al., "The Cyclohexasilanes $Si_6H_{11}X$ and $Si_6Me_{11}X$ with X=F, Cl, Br and I: A Quantum Chemical and Raman Spectroscopic Investigation of a Multiple Conformer Problem," Chem. Phys. Chem. 2007, vol. 8, pp. 735-744.

Kaczmarczyk et al., "A New Synthesis for Hexasilicon Tetradecachloride, $Si_6Cl_{14}$," Journal of American Chemical Society, vol. 82, 1960, pp. 751-752.

Kaczmarczyk et al., "A New Pentasilicon Dodecachlorida, $Si_5Cl_{12}$," Journal of Inorganic Nuclear Chemistry, 1961, vol. 17, pp. 186-188.

Norman et al., "The Lithium Tetraphosphinnoaluminate Phosphination of Halosilanes and Germanes," Inorganic Chemistry, 1970, vol. 9 (1), pp. 98-103.

Poschl et al., "Synthesis and Spectrosopy of Halogenated Cyclopentasilanes," Organometallics 1996, vol. 15, No. 14, pp. 3238-3240.

Sevast'Yanov et al., "Perchlorosilanes and Perchlorocarbosilanes as Precursors for SiC Synthesis," Inorganic Materials, vol. 43, No. 4, Pleiades Publishing, Inc. (2007), pp. 369-372.

Shono et al., "Electroreductive Synthesis of Polygermane and Germane-Silane Copolymer," J. Chem Soc., Chem Commun. 1992, pp. 896-897.

Tanaka et al., "Spin-on n-Type Silicon Films Using Phosphorous-doped Polysilanes," Japanese Journal of Applied Physics, vol. 46, No. 36, 2007, pp. L886-L888.

Vanderwielen et al., "An Examination of the Chlorination of Silanes by Silver Chloride," Inorganic Chemistry, vol. 11, No. 2, 1972, pp. 246-250.

Wiberg et al., Cleavage Reactions with the Chlorosilanes $Si_2Cl_6$, $Si_3Cl_8$, and $Si_5Cl_{12}$, Angew, Chem. Internation, Edit. vol. 1, 1962, No. 9, p. 517.

Wingeleth et al., "Redistribution of Primary Silyl—and Germyphosphines :Synthesis of Trisilyl—and Trigermylphosphines," Phosphorous and Sulfur and Related Elements, 1988, vol. 39 (1-2), pp. 123-129.

* cited by examiner

METHOD OF PRODUCING CYCLOHEXASILANE COMPOUNDS

CROSS REFERENCE TO RELATED APPLICATIONS

This patent application is a national stage of International Patent Application No. PCT/US2011/022360, filed on Jan. 25, 2011; which claims the benefit under 35 U.S.C. 119(e) of U.S. Provisional Application Ser. No. 61/299,287, filed Jan. 28, 2010, entitled "Method of Producing Cyclohexasilane Compounds," and U.S. Provisional Application Ser. No. 61/311,118, filed Mar. 5, 2010, entitled "Method of Producing Cyclohexasilane Compounds," the disclosures of which are herein incorporated by reference in their entirety for any and all purposes.

GOVERNMENT RIGHTS STATEMENT

This invention was made with government support under U.S. Department of Energy Grant No. DE-FG36-08GO88160. The government has certain rights in the invention.

BACKGROUND

Tetradecahalocyclohexasilane compounds, such as those represented by the formula $Y_m Si_6 X_{14-n} X'_n$ (Y=cations with a +1 charge and m=2, or a +2 charge and m=1; and X and X'=F, Cl, Br, I and n=0-13) are important intermediates in the production of cyclohexasilane, $Si_6 H_{12}$, and other silane compounds. Cyclohexasilane can be employed as a liquid precursor for electronics grade silicon materials and devices. Cyclohexasilane is a relatively benign, liquid phase alternative to gaseous $SiH_4$ and/or corrosive trichlorosilane ($HSiCl_3$) in the various processes and technologies adopted in silicon-based electronic industries. Existing methods of producing the $Y_2 Si_6 Cl_{14}$ intermediate salt typically use nucleophilic organic amines as ligands. Such syntheses are prone to extensive side reactions that deplete useful starting materials and give low yields of the intermediate $Y_2 Si_6 Cl_{14}$ salt (typically approximately 10%).

SUMMARY

The present application is directed to a method of preparing a cyclohexasilane compound from trichlorosilane. The method includes contacting trichlorosilane with a reagent composition to produce a compound containing a tetradecahalocyclohexasilane dianion, e.g., a tetradecachlorocyclohexasilane dianion. The reagent composition typically comprises (a) tertiary polyamine ligand, e.g., alkyl substituted polyalkylenepolyamine; and (b) deprotonating reagent, which includes a compound other than a polyamine ligand. The deprotonating reagent may include a tertiary amine having a pKa of at least about 10.5 and often 11 or higher. Depending on the reaction components and conditions, reaction times of 1 to 72 hours may commonly be employed, with relatively short reaction times (e.g., 2-10 hours) being desirable. The present method can provide greatly enhanced yields of the tetradecachlorocyclohexasilane dianion product.

In certain embodiments, the reagent composition may comprise (a) tertiary polyalkylenepolyamine; and (b) deprotonating reagent, such as a trialkyl amine having a pKa of at least about 10.5. The tertiary polyamine ligand may be a polyamine containing nitrogen atoms with only alkyl, aryl and/or aralkyl substituents (desirably alkyl and/or aralkyl). Examples of suitable tertiary polyalkylenepolyamines include pentaalkyldiethylenetriamines and tetraalkylethylenediamines, such as N,N,N',N'-tetraethylethylenediamine (TEEDA) and N,N,N',N",N"-pentaethyldiethylenetriamine (PEDETA), as well as N,N,N',N'-tetraalkyl-N"-benzyldiethylenetriamines, such as N,N,N',N'-tetraethyl-N"-benzyldiethylenetriamine.

The reagent composition may desirably include tertiary amine having a pKa of at least about 10.5. Suitable examples include tertiary amines having a pKa of at least about 10.5, where the tertiary amine is substituted with three alkyl, aryl and/or aralkyl substituent groups. For example, the reagent composition may include N,N-diisopropylalkylamine and/or N,N-diisobutylalkylamine, where the alkyl group is methyl, ethyl, n-propyl, isopropyl, n-butyl, sec-butyl and/or other branched/linear alkyl groups (desirably having no more than 6 carbon atoms). The tertiary amine may also be substituted with one or more aralkyl groups such as a benzyl and/or phenethyl. In some embodiments, the reagent composition may include a tri-n-alkylamine, where the n-alkyl groups typically have no more than 6 carbon atoms (e.g., triethylamine, tri-(n-propyl)amine and/or tri-(n-butyl)amine). Other examples of suitable tertiary amines include N,N,N',N'-tetraalkyl-1,8-naphalenediamines where the alkyl groups are desirably $C_1$-$C_6$ alkyl and preferably methyl (e.g., N,N,N',N'-tetramethyl-1,8-naphthalenediamine and/or N,N,N',N'-tetraethyl-1,8-naphthalenediamine).

In some embodiments, a deprotonating reagent such as a high pKa tertiary amine (e.g., a trialkylamine having a pKa of at least about 10.5) gives improved yields of tetradecahalocyclohexasilane dianion salt, e.g., tetradecachlorocyclohexasilane dianion salt, when used in combination with PEDETA as the polyamine ligand. This beneficial effect is also noted when a high pKa tertiary amine is used with TEEDA as the polyamine ligand in combination with a quaternary salt, such as a tetraarylphosphonium salt. In some instances, the use of a sterically-hindered, tertiary amine (e.g., EDIPA®) may be advantageous. The absence of a deprotonating reagent (e.g., a sterically-hindered, tertiary amine) in the reagent composition often gives low product yield (commonly <10%) due largely to the occurrence of unwanted side reactions.

Methods of converting the tetradecahalocyclohexasilane dianion-containing compound to cyclohexasilane or a dodecaorganocyclohexasilane are also provided. For example, the tetradecahalocyclohexasilane dianion-containing compound produced by the present method may be converted into cyclohexasilane through reaction with a metal hydride reducing agent. The tetradecahalocyclohexasilane dianion-containing compound may also be reacted with a reagent having a formula RMgX (wherein R is alkyl or aryl and X is a halide) to produce a dodecaorganocyclohexasilane compound.

DETAILED DESCRIPTION

The present application relates to the use of a deprotonating reagent, such as a relatively high pKa tertiary amine (e.g., N,N-diisopropylamine (EDIPA®)—a sterically-hindered, non-nucleophilic amine) and may also employ a quaternary counterion material, such as a phosphonium counterion material to decrease side-reactions and facilitate efficient precipitation of the desired tetradecachlorocyclohexasilane dianion product. This approach favors the forward reaction and can lead to dramatic enhancements in yields. During the course of experiments, an improvement in yields of 3× and higher (versus maximum yields of about 10% using previously reported methods) has been observed from action of EDIPA® on PEDETA.$H_2SiCl_2$ complex in dichloromethane solvent. When EDIPA® was directly added to the reaction of the tertiary polyamine, PEDETA, with $HSiCl_3$ in optimized ratios, the yield of the (PEDETA.$SiH_2Cl$)$_2$($Si_6Cl_{14}$) salt was improved by nearly an order of magnitude (65-85%) versus the ~10% yields realized with conventional processes. In some instances, quaternary salts (e.g., $R_n R'_{4-n} EX$ where n=1-

4, R, R'=H, alkyl, aryl; E=N, P, As, Sb, Bi) may be added to the reaction. For example, the use of TEEDA as the polyamine ligand and EDIPA® as the deprotonating reagent leads to a 7× or higher enhancement in the yield of tetradecachlorocyclohexasilane dianion salt ($Y_2Si_6Cl_{14}$) when $Ph_4PCl$ is used to introduce the counterion material. Another example of a suitable quaternary salt is a quaternary ammonium salt.

It has been demonstrated that a high pKa tertiary amine (e.g., EDIPA® or triethylamine (TEA)) can provide greatly enhanced yields of $Y_2Si_6Cl_{14}$ (e.g., 65-85%) when used with PEDETA as the polyamine ligand. Improved yields are also noted when a high pKa tertiary amine is used with TEEDA as the polyamine ligand in combination with a tetraarylphosphonium cation, such as tetraphenylphosphonium cation. The absence of a deprotonating reagent (i.e., the high pKa tertiary amines noted above) in the reagent composition often results in low $Y_2Si_6Cl_{14}$ yield (i.e., <10% commonly) due largely to the occurrence of unwanted side reactions.

Other examples of suitable tertiary polyamine ligands include tertiary polyalkylpoly-alkeneamines, tertiary polyalkylenepolyalkeneamines, tertiary polyarylpolyalkeneamines, tertiary polyaraalkylpolyeneamines and tertiary amines that have one or more silyl groups on the nitrogen. Suitable tertiary polyamine ligands may also include tertiary polyalkylenepolyamines that are substituted with a mixture of alkyl and/or aralkyl substituent groups on the nitrogen atoms. Examples include, but are not limited to, N,N,N',N'-tetraalkyl-N''-benzyldiethylene-triamines, such as N,N,N',N'-tetraethyl-N''-benzyldiethylenetriamine and related derivatives where the alkyl and/or benzyl groups are replaced with hydrocarbon or organosilicon groups.

Sterically-hindered tertiary amines such as EDIPA® are suitable for use as deprotonating reagents when used in combination with polyamines according to the present method. The sterically-encumbered nature and relatively high pKa (i.e., 11.3) of EDIPA® can enhance the efficiency of proton abstraction while limiting its role to act as a nucleophile. Both features are believed to limit the formation of unwanted side products such as silicon tetrachloride. The yields of the tetradecachlorocyclohexasilane dianion product may also be enhanced through the use of other tertiary amines to act as a high pKa, proton abstractor (i.e., deprotonating reagent) thereby allowing the tertiary polyamine (e.g., PEDETA) to function as a polydentate ligand.

Other examples of suitable high pKa tertiary amines include N,N-diisopropyl-aralkylamines, N,N-isopropyldiaralkylamines, N,N-diisopropylarylamines, N,N-diarylalkylamines, N,N,N-triarylamines and/or N,N,N-triaralkylamines, where such tertiary amines preferably have a pKa of at least about 10.5.

Other examples of suitable high pKa tertiary amines include alkylated cyclic amines such as N-alkyl piperazines, N-aralkyl-substituted piperazines, N-alkyl pyrrolidines and N-aralkyl-substituted pyrrolidines. The N-alkyl piperazines and N-alkyl pyrrolidines may desirably include a bulky alkyl group as a substituent on the nitrogen atom (e.g., N-isopropyl, N-isobutyl or N-cyclohexyl). The carbon atom(s) immediately adjacent the nitrogen atom in the cyclic amine may be substituted with one or more alkyl groups. Examples of suitable N-alkyl pyrrolidines include N-isopropylpyrrolidine, N-ethyl-2-methylpyrrolidine and N-benzyl-pyrrolidine. Examples of suitable N-alkyl piperazines include N-isopropylpiperazine, N-ethyl-2-methylpiperazine and N-phenethylpiperazine. Such tertiary, alkylated cyclic amines desirably have a pKa of at least about 10.5.

Other examples of suitable deprotonating reagents that may be employed in the present method include metal hydride reagents. For example, metal hydrides such as LiH, NaH, KH, $MgH_2$, $CaH_2$, $SrH_2$ and $BaH_2$ are known to be good deprotonating agents and may be used in place of or in conjunction with tertiary amine deprotonating reagents. In addition, alkali metal amides (i.e., $MNR_2$ where M=Li, Na, K and R=alkyl, aryl, araalkyl or organosilyl group) and alkaline earth amides (i.e., $M(NR_2)_2$ where M=Mg, Ca, Sr, Ba and R=alkyl, aryl, araalkyl or organosilyl group) may be used as deprotonating reagents. Typical examples of such metal amides are lithium diisopropylamide ($LiN(i-Pr)_2$) and sodium hexamethyldisilazide ($NaN(SiMe_3)_2$).

In the present method, the trichlorosilane can be contacted with the reagent composition in any standard reactor suitable for contacting a chlorosilane with another reactant. The reactor can be, for example, a continuous-stirred batch type reactor, a semi-batch type reactor or a continuous type reactor. In some embodiments, it may be advantageous to carry out the present reaction in a vessel that can be sealed, thereby minimizing the potential loss of volatile components during the course of the reaction. The use of a sealed reactor can also allow the reaction to be run at temperatures above the boiling point of the solvent or other components of the reaction mixture (e.g., $HSiCl_3$, by 32° C.).

The present method is preferably carried out under substantially anhydrous conditions. This can be accomplished by purging the reactor with a dry inert gas such as nitrogen or argon and thereafter maintaining a blanket of such inert gas in the reactor. Often all glassware items are cleaned and dried at 140-150° C. for at least several hours prior to use. All procedures may be performed under nitrogen and/or argon atmosphere using standard Schlenk techniques.

Although $Y_2Si_6Cl_{14}$ can be prepared via the present method in the absence of a diluent, the step of contacting trichlorosilane with the reagent composition is typically carried out in the presence of an organic solvent. Any organic solvent or mixture of organic solvents that does not interfere with the coupling reaction of trichlorosilane to form the tetradecachlorocyclohexasilane dianion can be used. The organic solvent may include haloorganic solvents such as chloroform, dichloromethane and/or 1,2-dichloroethane. Quite often, the organic solvent is dichloromethane and/or 1,2-dichloroethane. When present, the amount of organic solvent is typically 0.01-100 (preferably 0.5-10) times the volume of all combined reagents.

The trichlorosilane may be contacted with the reagent composition at temperatures from 0 to 120° C. with common reaction temperatures from 20 to 75° C. (preferably ~40 to 65° C.). Higher temperatures may be achieved under elevated pressures or in a higher boiling point solvent under reflux conditions. Trichlorosilane may be contacted with the reagent composition at a temperature of 15 to 75° C. and often about 25 to 65° C. In some embodiments, the trichlorosilane may be introduced into the reaction mixture at relatively low temperatures, e.g., from −40 to 25° C. After the addition of trichlorosilane is complete, the reaction is typically allowed to proceed at the higher temperatures noted above.

The compound containing the tetradecachlorocyclohexasilane dianion may be isolated from the reaction mixture by crystallization/precipitation. For example, recovery of the compound containing the tetradecachlorocyclohexasilane dianion can be achieved by adding sufficient quantities of organic solvents that promote crystallization. Crystallization may take place at or below room temperature. Alternatively, the compound containing the tetradecachlorocyclohexasilane dianion can be recovered from the reaction mixture by adding sufficient quantities of organic solvents that aid precipitation of the compound (e.g., by adding a hydrocarbon non-solvent to a solution of tetradecachlorocyclohexasilane dianion salt in chlorinated organic solvent). In some instances, it may be advantageous to use a blended solvent system. Such mixtures would utilize a chlorinated organic solvent (e.g., $CH_2Cl_2$ and/or $C_2H_4Cl_2$) and/or an aliphatic hydrocarbon (e.g., pentane, hexane and/or cyclohexane), and/ or an ether (e.g., diethyl ether and/or tetrahydrofuran) and/or an aromatic hydrocarbon (e.g., benzene and/or toluene) solvent.

Any organic solvent or mixture of such solvents that effects crystallization or precipitation of the compound containing the tetradecachlorocyclohexasilane dianion from the reaction mixture and does not react with the compound being recovered may be used in the present method. Examples of suitable organic solvents include hydrocarbons such as pentane, hexane, heptane, octane and nonane as well as ethers such as diethyl ether and tetrahydrofuran. Preferably, the organic solvents used for effecting crystallization or precipitation of the compounds produced by the present method are pentane, hexane, heptane, octane or nonane. One example of a particularly suitable solvent is pentane.

The tetradecahalocyclohexasilane dianion, such as a tetradecachlorocyclohexasilane dianion, can be chemically reduced to cyclohexasilane. The reduction reaction can be carried out by contacting the compound containing the tetradecahalocyclohexasilane dianion with a metal hydride reducing agent in an organic solvent at temperatures from −110 to 150° C. Suitable reducing agents include lithium aluminum hydride and diisobutylaluminum hydride.

The tetradecahalocyclohexasilane dianion, such as a tetradecachlorocyclohexasilane dianion, can also be contacted with a Grignard reagent to form a dodecaorganocyclohexasilane. The Grignard reagent is represented by the formula RMgX wherein R is alkyl or aryl and X is Cl, Br or I. Suitable R groups include, but are not limited to, methyl, ethyl, propyl, tert-butyl and phenyl. The reaction of the compound containing the tetradecahalocyclohexasilane dianion with Grignard reagents can be performed by standard methods known in the art for reacting chlorosilanes with Grignard reagents.

EXAMPLES

The following examples are presented to illustrate the present invention and to assist one of ordinary skill in making and using the same. The examples are not intended in any way to otherwise limit the scope of the invention. All yields are by weight percent unless otherwise noted. Unless otherwise specified, all procedures are performed under nitrogen atmosphere using standard Schlenk techniques or in a carefully dried and nitrogen filled glovebox. All glassware items are properly cleaned and dried at 140-150° C. for at least two hours before use.

Comparison Example 1

Synthesis of $(PEDETA.SiH_2Cl)_2(Si_6Cl_{14})$ without Deprotonating Reagent

A 3 L three neck round-bottomed flask (previously dried in an oven at 140° C.) equipped with a magnetic stirrer and a Friedrichs condenser was flushed with nitrogen. The flask was charged with dichloromethane (400 mL) followed by N,N,N',N'',N''-pentaethyldiethylenetriamine (PEDETA, 115.4 g, 474 mmol). To this mixture, trichlorosilane (250 mL, 1.37 mol) was added dropwise over a period of one hour. An exotherm was observed during the addition and vapor was condensed back into the flask (Friedrichs condenser coolant temperature is maintained at −10° C.). After the exotherm subsided, the reaction mixture was stirred at reflux (~45° C.) under a nitrogen atmosphere for 72 h. At the end of this period, heating was discontinued and the precipitate was allowed to settle. The reaction mixture was filtered using suction and the resulting product washed with dichloromethane (200 mL) giving 30 g (23.4 mmol) colorless solid (9.8% yield based on PEDETA).

Comparison Example 2

Synthesis of $(Ph_4P)_2(Si_6Cl_{14})$ without Deprotonating Reagent

N,N,N',N'-tetraethylethylenediamine (TEEDA) (1.09 mL, 5.11 mmol) was added to a solution of tetraphenylphosphonium chloride ($Ph_4PCl$, 1.87 g, 4.99 mmol) in 10 mL dichloromethane. Using a chilled syringe, trichlorosilane (2.02 mL) was slowly added to the stirring solution. The reaction solution was refluxed for 72 h in which time the product precipitated out as a colorless solid. The solid was filtered, washed with dichloromethane, and dried for 3 h under high vacuum to obtain $(Ph_4P)_2(Si_6Cl_{14})$ salt (0.687 g, 20.4%).

Example 1

Synthesis of $(PEDETA.SiH_2Cl)_2(Si_6Cl_{14})$ with Deprotonating Reagent

A 3 L three neck round-bottomed flask equipped with a magnetic stirrer and a Friedrichs condenser were flushed with nitrogen. The flask was then charged with dichloromethane (400 mL) followed by PEDETA (81.5 g, 320 mmol) and EDIPA® (143 g, 1.10 mol). Trichlorosilane (187 mL, 1.85 mol) was added drop-wise to this mixture over a period of 1 h with the vapor formed by the exotherm being condensed back into the flask (Friedrichs condenser coolant temperature maintained at −10° C.). After addition, the reaction mixture was stirred at reflux (~45° C.) under a nitrogen atmosphere for 42-72 h. At the end of this period, heating was discontinued and the colorless precipitate was filtered using suction. The resultant product was washed with 100 mL dichloromethane under nitrogen giving 165 g (128 mmol) of $(PEDETA.SiH_2Cl)_2(Si_6Cl_{14})$ in 81% yield (based on PEDETA).

Example 2

Synthesis of $(Ph_4P)_2(Si_6Cl_{14})$ with EDIPA® as Deprotonating Reagent

TEEDA (1.09 mL, 5.11 mmol) and EDIPA® (2.61 mL, 15.0 mmol) were added to a solution of $Ph_4PCl$ (1.88 g, 5.02 mmol) in 20 mL dichloromethane. Using a chilled syringe, trichlorosilane (3.10 mL, 30.7 mmol) was added slowly to the stirring solution. With the addition of the chlorosilane, the solution warmed and turned slightly yellow in color. The reaction solution was refluxed for 72 h during which time the product precipitated as a colorless solid. The solid was filtered, washed with dichloromethane, and dried for 3 h under vacuum giving 2.37 g $(Ph_4P)_2(Si_6Cl_{14})$ in 70.3% yield (based on $Ph_4PCl$).

Example 3

Synthesis of $(Ph_4P)_2(Si_6Cl_{14})$ with Triethylamine as Deprotonating Reagent TEEDA (1.10 mL, 5.16 mmol) and triethylamine (2.09 mL, 15.0 mmol) were added to a solution of $Ph_4PCl$ (1.88 g, 5.02 mmol) in 20 mL dichloromethane. Using a chilled syringe, trichlorosilane (3.10 mL, 30.7 mmol) was slowly added to the stirring solution. During addition, a gel-like solid formed that slowly dissolved with stirring. The reaction was refluxed for 72 h. The colorless precipitate was filtered, washed with dichloromethane and then dried for 3 h under vacuum giving 2.20 g $(Ph_4P)_2(Si_6Cl_{14})$ in 65.6% yield (based on $Ph_4PCl$).

Example 4

Synthesis of Tetradecachlorocyclohexasilane Dianion Salts—Solvent Variations

Reactions were performed using 1,2-dichloroethane and acetonitrile in addition to dichloromethane to study the effect of solvent polarity on yield. The results of this study are given in Table 1 where the reactions were performed according to the following protocol. PEDETA (2.00 g, 8.22 mmol) and EDIPA® (3.19 g, 24.7 mmol) were diluted with dry solvent (11 mL) and transferred to a 20 mL reaction vial containing a PTFE-coated magnetic stir bar. The reaction vial containing the amine solution was sealed with a rubber septum and cooled to −30° C. While stirring, trichlorosilane (4.15 mL, 41.1 mmol) was added to the amine solution though the septum using a chilled syringe. The resulting solution was cooled to −30° C. and the septum on the reaction vial was quickly replaced with a medium pressure (20 bar) crimp cap. The reaction mixtures were then heated to 55-60° C. for 7 h. The product mixtures were cooled to −30° C. for 23 h after the reaction period. After isolation by vacuum filtration and rinsing with $CH_2Cl_2$, product yields >40% were observed for the reactions performed in 1,2-dichloroethane, acetonitrile and $CH_2Cl_2$.

TABLE 1

Effect of Solvent on Reaction Yield

| Solvent | Yield |
|---|---|
| 1,2-Dichloroethane | 57% |
| Acetonitrile | 43% |
| $CH_2Cl_2$ | 46% |
| $CH_2Cl_2$ | 48% |

Example 5

Synthesis of Tetradecachlorocyclohexasilane Dianion Salts—Mixed Solvents

In some instances, it may be advantageous to use a blended solvent system. Such mixtures would utilize a chlorinated organic solvent (e.g., $CH_2Cl_2$ and/or $C_2H_4Cl_2$) and/or an aliphatic hydrocarbon (e.g., pentane, hexane and/or cyclohexane), and/or an ether (e.g., diethyl ether and/or tetrahydrofuran) and/or an aromatic hydrocarbon (e.g., benzene and/or toluene). Reactions were performed using dichloromethane-based mixtures with benzene, tetrahydrofuran and cyclohexane. The results of this study are given in Table 2 where the reactions were performed according to the following protocol. PEDETA (0.5 g, 2.06 mmol) and EDIPA® (0.8 g, 6.19 mmol) were mixed in a 5 mL reaction vial with a stir bar and diluted with dry dichloromethane (2.5 mL) and dry secondary solvent (0.5 mL). The reaction vessel was capped with a rubber septum and cooled to −30° C. Trichlorosilane (1.05 mL) was added to the reaction vessel though the septum using a chilled syringe. The reaction vessel was cooled to −30° C. before the rubber septum was quickly replaced with a medium pressure (20 bar) crimp cap. The reaction vessel was then placed in a heated oil bath at 55-60° C. for 7 h with stirring. After isolation by vacuum filtration and rinsing with $CH_2Cl_2$, product yields >40% were observed for all the mixed solvent reactions (Table 2).

TABLE 2

Effect of Mixed Solvents on Reaction Yield

| Solvent | Yield |
|---|---|
| 5:1 $CH_2Cl_2$/Benzene | 48% |
| 5:1 $CH_2Cl_2$/Tetrahydrofuran | 43% |
| 5:1 $CH_2Cl_2$/Cyclohexane | 47% |

Example 6

Synthesis of Tetradecachlorocyclohexasilane Dianion Salts—General Modifications

The time for producing $Si_6Cl_{14}^{2-}$ salts can be reduced from the usual 42-72 h described in the examples above to about 7 h using a number of alternate reaction conditions. The general approach was to conduct the reaction in a sealed reaction vessel capable of withstanding medium pressures (up to about 20 bar). Energy/heat was introduced to the reaction mixture using a variety of methods as described below with control reactions performed at room temperature for 5 days. The general reaction scheme, unless otherwise specified, is as given below:

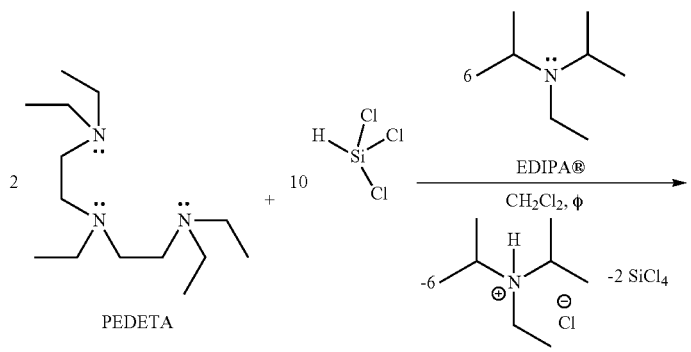

-continued

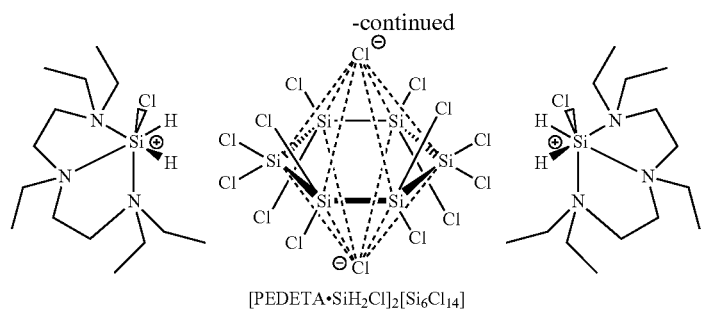

[PEDETA·SiH₂Cl]₂[Si₆Cl₁₄]

φ = heat (60° C.), microwave, ultrasound, room temperature

The stoichiometry for the reaction can be summarized as follows:

2PEDETA+6EDIPA+10HSiCl₃→[PEDETA.SiH₂Cl]₂[Si₆Cl₁₄]+2SiCl₄+6EDIPA.HCl

A typical procedure for the modified reactions is now given. This is the general procedure that was used for all samples described in Table 3. PEDETA (2.00 g, 8.22 mmol) and EDIPA® (3.19 g, 24.7 mmol) were diluted with dry dichloromethane (11 mL) and transferred to a 20 mL reaction vial containing a PTFE-coated magnetic stir bar. The reaction vial containing the amine solution was sealed with a rubber septum and cooled to −30° C. While stirring, trichlorosilane (4.15 mL, 41.1 mmol) was added to the amine solution though the septum using a chilled syringe. The resulting solution was cooled to −30° C. and the septum on the reaction vial was quickly replaced with a medium pressure (20 bar) crimp cap. The solution was heated for various periods using an oil bath maintained at 60° C. for conventional thermal reactions. In separate experiments, similar solutions were placed in a Biotage Initiator microwave or a conventional ultrasonic cleaning bath. One of the experiments used TEEDA and PPh₄Cl as the ligand and the counter ion source, respectively, instead of PEDETA. For each experiment listed in Table 3, the product mixtures were cooled to −30° C. for 23 h after the reaction period. Sonochemical reactions and room temperature control experiments were performed at one-quarter scale using ~0.5 g PEDETA, ~0.8 g EDIPA® and ~1.0 g trichlorosilane.

The results for the general modification experiments are summarized below in Table 3. In most instances, more product precipitates from the filtrates after extended periods of time yielding second crops of crystals. Isolated yields from 40-60% were typically observed after reaction for 7 h at 40-60° C. Extended reaction times were required to obtain comparable yields for reactions at room-temperature. The effect of sonication was probed by performing a ¼ scale reaction at 0° C. using a standard ultrasonic bath. No product was observed during sonication, but precipitate was observed after standing overnight at 23° C. The identical sonochemical reaction performed at 50° C. gave a 32% yield after 7 h.

TABLE 3

Summary of the Conditions for Microwave and Thermal Experiments.

| Entry | Time (h) | Max Temp | Yield (%) | Rxn Type |
|---|---|---|---|---|
| 1 | 2 | 60 | 27 | Microwave |
| 2 | 2 | 60 | 29 | Thermal |
| 3 | 6.8 | 60 | 44 | Microwave |
| 4 | 7 | 60 | 46 | Microwave |

TABLE 3-continued

Summary of the Conditions for Microwave and Thermal Experiments.

| Entry | Time (h) | Max Temp | Yield (%) | Rxn Type |
|---|---|---|---|---|
| 5 | 7 | 60 | 48 | Thermal |
| 6 | 10 | 60 | 46 | Microwave |
| 7 | 16 | 60 | 47 | Microwave |
| 8 | 16 | 60 | 54 | Thermal |
| 9[a] | 7 | 60 | 47 | Microwave |
| 10 | 48 | 60 | 45 | Thermal |
| 11 | 72 | 60 | 42 | Thermal |
| 12 | 6 | 80 | 23 | Microwave |
| 13 | 2 | >110 | 0 | Microwave |
| 14 | 117 | 23 | 46 | Thermal |

[a]This reaction was run with TEEDA as the polyamine and Ph₄PCl as the cation source.

Illustrative Embodiments

Reference is made in the following to a number of illustrative embodiments of the subject matter described herein. The following embodiments illustrate only a few selected embodiments that may include the various features, characteristics, and/or advantages of the subject matter as presently described. Accordingly, the following embodiments should not be considered as being comprehensive of all of the possible embodiments.

According to one embodiment, a cyclohexasilane compound may be prepared by a method comprising contacting trichlorosilane with a reagent composition, which comprises (a) tertiary polyamine, e.g., tertiary polyalkylenepolyamine; and (b) tertiary amine having a pKa of at least about 10.5 to produce a compound containing a tetradecahalocyclohexasilane dianion, such as a tetradecachlorocyclohexasilane dianion. The reaction mixture typically comprises tertiary polyamine ligand, deprotonating reagent and trichlorosilane in a molar ratio of tertiary polyamine ligand:deprotonating reagent:trichlorosilane from 1:3:3 to 1:400:700. In certain embodiments, it may be desirable to employ a reaction mixture, which comprises tertiary polyalkylenepolyamine, trialkylamine and trichlorosilane in a the mole ratio of tertiary polyalkylenepolyamine:trialkylamine:trichlorosilane from 1:3:3 to 1:400:700. In certain embodiments, it may be desirable to employ a reaction mixture, which comprises the tertiary polyalkylenepolyamine, the trialkylamine and trichlorosilane in a the mole ratio of tertiary polyalkylenepolyamine:trialkylamine:trichlorosilane from 1:3:5 to 1:30:50.

According to another embodiment, a cyclohexasilane compound may be prepared by a method comprising contacting trichlorosilane with a reagent composition, which comprises (a) nucleophilic tertiary polyamine; (b) sterically-hindered, non-nucleophilic amine to produce a compound containing a tetradecachlorocyclohexasilane dianion (e.g., $(PEDETA \cdot SiH_2Cl)_2(Si_6Cl_{14})$ or $(R_nR'_{4-n}EX)_2(Si_6Cl_{14})$ where n=1-4, R, R'=H, alkyl, aryl; E=N, P, As, Sb, Bi).

According to another embodiment, the present method includes contacting trichlorosilane with a reagent composition comprising (a) tertiary polyamine ligand; and (b) high pKa tertiary amine (e.g., a tertiary amine having a pKa of at least 10.5). The tertiary polyamine ligand may include tertiary polyalkylenepolyamine. The tertiary amine may include sterically-hindered, non-nucleophilic amines such as N,N-diisopropylalkylamine and/or an N,N-diisobutylalkylamine. The tertiary polyamine ligand may be a fully alkylated polyamine, such as a pentaalkyldialkylenetriamine, tetraalkylalkylenediamine or hexaalkyltrialkylene-tetraamine where the alkyl groups are preferably $C_1$-$C_6$ alkyl. For example, the tertiary polyamine ligand may include N,N,N', N'',N''-penta(n-alkyl)diethylenetriamine and/or N,N,N',N'-tetra(n-alkyl)ethylenediamine. Particularly suitable examples of pentaalkyldiethylenetriamines and tetraalkylethylenediamines for use in the present method include N,N,N', N'-tetraethylethylenediamine (TEEDA) and N,N,N',N'',N''-pentaethyl-diethylenetriamine (PEDETA).

The reagent composition may further comprise a quaternary salt, such as a tetraarylphosphonium salt (e.g., a tetraarylphosphonium halide). Suitable examples of tetraarylphosphonium salts for use in the present method comprise tetraphenylphosphonium halides (e.g., $Ph_4PCl$, $Ph_4PBr$ and/or $Ph_4PI$). When the reagent composition comprises tetraarylphosphonium salt, the tetradecachlorocyclohexasilane dianion-containing reaction product may be isolated as a tetraarylphosphonium salt, such as the compound having the formula $(Ph_4P)_2(Si_6Cl_{14})$. The reaction mixture typically comprises the quaternary salt, tertiary polyamine ligand, deprotonating reagent and trichlorosilane in a molar ratio of quaternary salt:tertiary polyamine ligand:deprotonating reagent:trichlorosilane from 1:1:3:5 to 100:1:400:600. In certain embodiments, it may be desirable to employ a reaction mixture, which comprises the quaternary salt, tertiary polyalkylenepolyamine, tertiary amine (e.g., trialkylamine) and trichlorosilane in a molar ratio of quaternary salt:tertiary polyalkylenepolyamine:tertiary amine:trichlorosilane from 1:1:3:5 to 100:1:400:600. In certain embodiments, it may be desirable to employ a reaction mixture, which comprises tetraarylphosphonium chloride, N,N,N',N'-tetraalkylethylenediamine, trialkylamine and trichlorosilane in a molar ratio of tetraarylphosphonium chloride:N,N,N',N'-tetraalkylethylenediamine:trialkylamine:trichlorosilane from 1:1:3:5 to 1:30:40:60.

According to another embodiment, the present method includes contacting trichlorosilane with a reagent composition to form a compound containing a tetradecahalocyclohexasilane dianion, such as a tetradecachlorocyclohexasilane dianion, where the reagent composition comprises (a) tertiary polyamine ligand; and (b) high pKa tertiary amine. The tetradecachlorocyclohexasilane dianion-containing compound may be contacted with a reagent having a formula RMgX (wherein R is alkyl or aryl and X is chloro, bromo, or iodo) to produce dodecaorganocyclohexasilane $(Si_6R_{12})$.

According to another embodiment, the present method includes contacting trichlorosilane with a reagent composition to form a compound containing a tetradecahalocyclohexasilane dianion, such as a tetradecachlorocyclohexasilane dianion, where the reagent composition comprises (a) a tertiary polyamine ligand and (b) a high pKa tertiary amine. The tetradecahalocyclohexasilane dianion-containing compound may be contacted with a metal hydride reducing agent (e.g., lithium aluminum hydride or diisobutylaluminum hydride) to produce cyclohexasilane $(Si_6H_{12})$.

It will be readily apparent to one skilled in the art that varying substitutions and modifications may be made to the methods and compositions disclosed herein without departing from the scope and spirit of the invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

What is claimed:

1. A method of preparing a cyclohexasilane compound comprising:
   contacting trichlorosilane with a reagent composition to produce a compound containing a tetradecahalocyclohexasilane dianion, wherein the reagent composition comprises (a) tertiary polyamine ligand; and (b) deprotonating reagent, which comprises tertiary amine having a pKa of at least about 10.5;
   wherein the tertiary amine is a tertiary amine substituted with three alkyl and/or aralkyl substituents, a tertiary alkylated cyclic amine and/or an N,N,N',N'-tetraalkyl-1,8-naphthalenediamine.

2. The method of claim 1 wherein the tertiary polyamine ligand comprises tertiary polyalkylenepolyamine; and (b) the tertiary amine comprises trialkylamine.

3. The method of claim 1 wherein the tertiary polyamine ligand comprises N,N,N',N'',N''-pentaalkyldiethylenetriamine, N,N,N',N'-tetraalkylethylenediamine or a mixture thereof.

4. The method of claim 1 wherein the N,N,N',N'-tetraalkyl-1,8-naphthalenediamine is N,N,N',N'-tetramethyl-1,8-naphthalenediamine.

5. The method of claim 1 wherein the reagent composition further comprises a tetraarylphosphonium salt.

6. The method of claim 5 wherein the tetradecahalocyclohexasilane dianion-containing compound has a formula $(Ph_4P)_2(Si_6Cl_{14})$.

7. The method of claim 5 wherein the reagent composition comprises tetraarylphosphonium chloride, N,N,N',N'-tetraalkylethylenediamine, trialkylamine and trichlorosilane in a molar ratio of tetraarylphosphonium chloride:N,N,N',N'-tetraalkylethylenediamine:trialkylamine:trichlorosilane from 1:1:3:5 to 100:1:400:600.

8. The method of claim 1 wherein the tertiary amine comprises N,N-diisopropylethylamine, triethylamine or a mixture thereof; and the tertiary polyamine ligand comprises tertiary polyalkylenepolyamine.

9. The method of claim 2 wherein the reagent composition comprises the tertiary polyalkylenepolyamine, the trialkylamine and the trichlorosilane in a mole ratio of tertiary polyalkylenepolyamine:trialkylamine:trichlorosilane from 1:3:3 to 1:400:700.

10. The method of claim 1 wherein the tertiary polyamine ligand comprises N,N,N',N'',N''-pentaethyldiethylenetriamine (PEDETA) and the deprotonating reagent comprises N,N-diisopropylethylamine.

11. The method of claim 1 wherein the tertiary polyamine ligand comprises N,N,N',N'',N''-pentaethyldiethylenetriamine and the deprotonating reagent comprises triethylamine.

12. The method of claim 1 wherein the tertiary polyamine ligand comprises N,N,N',N'-tetraethylethylenediamine; the deprotonating reagent comprises N,N-diisopropylethylamine, triethylamine or a mixture thereof; and the reagent composition further comprises tetraphenylphosphonium chloride.

13. The method of claim 1 wherein the tetradecahalocyclohexasilane dianion-containing compound has a formula $(PEDETA \cdot SiH_2Cl)_2(Si_6Cl_{14})$.

14. The method of claim 1, wherein contacting the trichlorosilane with the reagent composition is carried out in the presence of an organic solvent comprising chlorinated organic solvent.

15. The method of claim 1 further comprising recovering the tetradecahalocyclohexasilane dianion containing-compound.

16. The method of claim 15 wherein recovering the tetradecahalocyclohexasilane dianion-containing compound is achieved by filtration of a precipitate formed during the reaction.

17. The method of claim 15 further comprising contacting the tetradecahalocyclohexasilane dianion-containing compound with a reagent having a formula RMgX, wherein R is alkyl or aryl and X is chloro, bromo, or iodo to produce a dodecaorganocyclohexasilane.

18. The method of claim 15 further comprising contacting the tetradecahalocyclohexasilane dianion-containing compound with a metal hydride reducing agent to produce cyclohexasilane.

19. The method of claim 1 wherein the tertiary amine comprises N,N-diisopropylalkylamine, N,N-diisobutylalkylamine, triethylamine, tri-n-propylamine, tri-n-butylamine or a mixture thereof; the tertiary polyamine ligand comprises N,N,N',N'',N''-pentaethyldiethylene-triamine or N,N,N',N'-tetraethylethylenediamine.

20. The method of claim 1 wherein the tertiary polyamine ligand comprises N,N,N',N'-tetraalkyl-N''-benzyldiethylenetriamine.

* * * * *